United States Patent
Pompei et al.

(10) Patent No.: US 6,329,339 B1
(45) Date of Patent: Dec. 11, 2001

(54) PHARMACEUTICAL ANTIVIRAL COMPOSITION COMPRISING GLYCYRRHIZIC ACID AND AT LEAST ONE PROTEIN ENDOWED WITH ANTIVIRAL ACTIVITY

(75) Inventors: Raffaello Pompei, Quartu Sant'Elena; Mario Pinza, Corsico, both of (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 09/423,611

(22) PCT Filed: May 6, 1998

(86) PCT No.: PCT/EP98/02797
§ 371 Date: Jan. 18, 2000
§ 102(e) Date: Jan. 18, 2000

(87) PCT Pub. No.: WO98/51334

PCT Pub. Date: Nov. 19, 1998

(30) Foreign Application Priority Data

May 14, 1997 (IT) .................................. MI97A1119

(51) Int. Cl.[7] ........................... A61K 38/00; A61K 31/70
(52) U.S. Cl. .................................. 514/12; 514/33
(58) Field of Search .......................... 514/12, 33

(56) References Cited

PUBLICATIONS

Fukahori et al, Japanese Patents Abstracts, No. JP403145432A, Jun. 1991.*

* cited by examiner

*Primary Examiner*—William R. A. Jarvis
(74) *Attorney, Agent, or Firm*—Oblon, Spivak, McClelland, Maier & Neustadt, P.C.

(57) ABSTRACT

This invention relates to pharmaceutical compositions of and methods of treating viral infections with a synergistic combination of glycyrrhizic acid and either a lactoferrin or a lysozyme.

18 Claims, No Drawings

PHARMACEUTICAL ANTIVIRAL COMPOSITION COMPRISING GLYCYRRHIZIC ACID AND AT LEAST ONE PROTEIN ENDOWED WITH ANTIVIRAL ACTIVITY

This application is a 371 of PCT/EP98/02,797, filed May 6, 1998.

This invention relates to a pharmaceutical antiviral composition comprising glycyrrhizic acid and at least one protein endowed with antiviral activity.

It is known that the Herpes Simplex Virus type 1 causes facial and oropharyngeal lesions ("Manual of Clinical Microbiology", Murray, Baron, Pfaller, Tenover, Yolken, 6$^{th}$ edition, pages 876–883, American Society for Microbiology, Washington D.C., 1993).

In the past infections from Herpes Simplex Virus type 1 were treated with vidarabin (Goodman & Gilman, "Le basi farmacologiche della terapia", Zanichelli, Bologna, 7$^{th}$ ed., page 1156, 1991) but this has been almost completely replaced by aciclovir (Goodman & Gilman, "The Pharmacological Basis of Therapeutics", McGraw Hill Companies, 9$^{th}$ ed., chapter 50, page 1193, 1996; "Am. J. Med.", 73, Suppl., 186–192, 1982 and "Clin. Pharmacokinet.", 8, 187–201, 1983) because of its toxicity.

Currently, aciclovir is therefore the most used drug in the treatment of mouth and lip lesions (rash from fever) but its topical use often causes burning and irritation of mucous membranes. Moreover, aciclovir is fairly efficient when administered during the first infection, but is not very effective in the case of recurring infections, thus being non-resolutive and not preventing re-infection by Herpes Simplex Virus type 1.

Additionally, oral treatment has the disadvantage of causing side effects such as: nausea, diarrhoea, itching, headaches, renal inadequacies and nephrotoxicity.

Therefore, there is still a real need for a drug which is active in the treatment of infections from Herpes Simplex Virus type 1 even in the case of recurring infections and which is free from side effects.

Indeed, it has also been known that glycyrrhizic acid shows a certain antiviral activity. At antiviral doses, it largely inhibits the synthesis of viral glycoproteins and only at very high doses does it also inhibit the cell glycoproteins synthesis. In fact while the action of the glycyrrhizic acid on the synthesis of proteins, both in normal cells and infected cells, is practically irrelevant even at doses of 4 mM, the synthesis of glyco-proteins shows a substantial difference in normal and infected cells. In fact, at the concentration of 0.5 mM (which inhibits 50% of viral replication) glycyrrhizic acid causes a reduction in the incorporation of glucosamine-H$^3$ of more than 10% in infected cells and no inhibition in normal cells. An increased dose of glycyrrhizic acid up to 1 mM, causes an 80% reduction of the virus, no inhibition of the synthesis of glyco-proteins in the control and a 20% reduction in the synthesis of glyco-protein in infected cells. At 4 mM, the synthesis of glyco-proteins in the normal cells is also slightly altered, but the production of the virus is inhibited by 99% ("L'Igiene Moderna", Pompei R. and Marcialis M. A., 83, 385–391, 1985).

Furthermore, Table A shows the results of tests carried out treating cells infected by HSV1 with 8 mM glycyrrhizic acid. The infected cells have been kept in contact with the glycyrrhizic acid for 2 hours at 37° C. The experimental results given in the Table show that there is a strong decrease in infection at 12, 17 and 22 hours and that the cells retain their cellular integrity. The inhibition is of about 2 logarithms at 12 hours from the infection and 3 logarithms (99.9%) at 22 hours from infection ("Nature", Pompei R. et al., 281, No. 5733, 689–690,1979).

TABLE A

| | Viral production (PFU*/ml) after the following hours | | |
|---|---|---|---|
| Hours | 12 | 17 | 22 |
| Control | $3 \times 10^6$ | $5.4 \times 10^6$ | $2.6 \times 10^7$ |
| Glycyrrhizic acid 8 mM | $4.2 \times 10^4$ | $1.2 \times 10^4$ | $1.1 \times 10^4$ |

*PFU = plaque forming viral unit.

It is also known in the literature the antiviral activity and, more specifically, anti-herpetic (HSV1) activity of various types of lysozymes such as turkey lysosyme, human lysozyme, chicken lysozyme, denaturated (heat-inactivated) chicken lysozyme and chicken lysozyme digested with trypsin ("Current Microbiology", Cisani et al., 10, 35–40, 1984).

Lysozymes are, in fact, enzymes which are widely spread in nature and cooperate in the defense of the organism against some infecting agents by causing or cooperating to the cleavage (i.e. lysis) thereof ("Mol. Cell. Biochem.", Jolles et al., 63, 165–189, 1984; "Anticancer Res.", Save et al., 9, 583–592, 1989).

Moreover, in the literature it is described the antiviral activity and, more particularly, the antiherpetic (HSV1) activity of lactoferrin (Fujihara T. and Hayashi H. "Lactoferrin inhibits herpes simplex virus type 1 (HSV1) infection to mouse cornea", "Arch. Virol.", 140, 1469–1472, 1995; Harmsen MC. et al. "Antiviral effects of plasma and milk protein: lactoferrin shows potent activity against both human immunodeficiency virus and human cytomegalovirus replication in vitro", "J. Inf. Dis.", 172, 380–388,1994).

It has now surprisingly been found that glycyrrhizic acid has a synergetic effect on the proteins endowed with antiviral activity.

Therefore, it is a first object of this invention to provide a pharmaceutical composition characterized in that it comprises glycyrrhizic acid and at least one protein having antiviral activity.

Preferably, the protein is selected from the group comprising the lysozymes and the lactoferrins.

Typical examples of lysozymes are turkey lysozyme, human lysozyme, chicken lysozyme, heat-inactivated chicken lysozyme and chicken lysozyme digested with trypsin. Preferably, the lysozyme is a chicken lysozyme or a human lysozyme.

Typical examples of lactoferrins are bovine and human lactoferrins.

Typically, the pharmaceutical composition of this invention is useful in the treatment of topical viral infections. Preferably, the virus is of a herpetic type. Even more preferably it is the Herpes Simplex Virus type 1 (HSV1).

Preferably, the pharmaceutical compositions of this invention are prepared in the form of suitable dosage forms. Examples of suitable dosage forms are creams, ointments and medicated plasters, for topical administration.

The dosage forms may also contain other conventional ingredients, such as: preservatives, stabilisers, surfactants, buffers, salts to regulate osmotic pressure, emulsifiers, sweeteners, colouring agents, flavouring agents and the like.

The amount of active ingredients in the pharmaceutical composition of this invention may vary within a wide range depending on known factors such as, for example, stage and severity of the infection, body weight of the patient, type of the dosage form, administration route, number of dosage forms administered per day and the efficacy of the active ingredients. However, the optimum amount will be determined readily and routinely by a person skilled in the art.

Preferably, the amount of glycyrrhizic acid, a lysozyme and/or a lactoferrin in the dosage form of this invention will be such that it ensures a daily administration of 0.25–8 mg/ml of glycyrrhizic acid, 0.5–10 mg/ml of lysozyme and/or 0.1–4 mg/ml of lactoferrin. Even more preferably, it will be such that it ensures a daily administration of 0.5–2 mg/ml of glycyrrhizic acid, 0.5–4 mg/kg of lysozyme and/or 0.25–1 mg/kg of lactoterrin. The dosage forms of the pharmaceutical composition of this invention may be prepared according to techniques which are well known to the pharmaceutical chemist, and comprise mixing, granulation, compression, dissolution and the like.

The following examples are intended to illustrate this invention without limiting it in any way.

The compounds used in the experiments were:
glycyrrhizic acid (as ammonium salt) supplied by FLUKA AG;
Herpes Simplex Virus type 1 supplied by the NIH, Rockville, Md.;
chicken lysozyme supplied by SIGMA;
lactoferrin supplied by SIGMA;
VERO cell from kidney of African green monkey from ICN FLOW, Costa Mesa, Calif.;
Eagle medium modified by Dulbecco (DMEM), added with calf foetal serum, inactivated for 30' at 56° C., supplied by ICN FLOW, Costa Mesa, Calif.

EXAMPLE 1

Single cell layers of VERO cells were plated on 24 wells plates and infected with about 1 HSV1 viral infecting unit x 100 cells for one hour at room temperature. Then different amounts from 0 to 8 mg/ml of chicken, turkey and human lysozymes were added in a thermostat at 37° C. and in the presence of $CO_2$ (5%).

After 48 hours, when the cytopathic effect was total in the control, the cells were frozen and defrosted twice to cause rupture and, therefore, the release of the virus.

The concentration of infecting viral particles produced for each dilution of lysozyme was titrated after centrifugation. Titration was carried out by diluting the content of each well from $10^{-1}$ to $10^{-7}$ and putting it in contact with single layer cells in a multiwell having 6 wells each for 1 hour at room temperature.

Once the infection had occurred, the cells were covered with an earth of nutritive agar and, after 48 hours of incubation, they were coloured with red neutral, and the macroscopically visible viral plaques were counted. Thus the inhibition percentage obtained on the viral plaque by lysozyme compared with the control was established.

The experimental data obtained in this way are given in Table 1.

TABLE 1

Inhibition (%) of viral plaques with various lysozymes

| Doses (mg/ml)* | 0 | 8 | 6 | 4 | 2 | 1 | 0.5 |
|---|---|---|---|---|---|---|---|
| Chicken | 0 | 93 ± 3 | 82 ± 4 | 71 ± 6 | 60 ± 6 | 49 ± 5 | 20 ± 4 |
| Turkey | 0 | 89 ± 5 | 80 ± 4 | 68 ± 5 | 55 ± 6 | 45 ± 5 | 10 ± 3 |
| Human | 0 | 90 ± 5 | 79 ± 6 | 70 ± 4 | 59 ± 4 | 45 ± 3 | 18 ± 3 |

*Percentage of the control ± standard deviation.

Table 1 shows that:
1) chicken lysozyme
   i) significantly inhibits the formation of herpetic virus plaques on VERO cells;
   ii) the action is dose-dependent;
   iii) at the dose of 8 mg/ml inhibits HSV1 of about 92%;
   iv) the 50% inhibiting dose (ID50) is of about 1 mg/ml;
2) the turkey and human lysozymes showed an antiherpetic activity similar to chicken lysozyme.

EXAMPLE 2

It was carried out as Example 1 except that different amounts of from 0 to 1 mg/ml of sole glycyrrhizic acid were added to the single layers of VERO cells infected with HSV1. The experimental results are shown in Table 2.

TABLE 2

Glycyrrhizic acid - Inhibition (%) of viral plaques

| Doses (mg/ml) | 0.2 | 0.4 | 0.6 | 0.8 | 1 |
|---|---|---|---|---|---|
| Inhibition (%) | 0 | 10 ± 4 | 27 ± 7 | 50 ± 8 | 75 ± 12 |

EXAMPLE 3

It was carried out as Example 1 except that 0.5 mg/ml of glycyrrhizic acid and different amounts of chicken lysozyme of from 0 to 1 mg/ml were added to the single layers of VERO cells infected with HSV1.

The experimental results are shown in Table 3.

TABLE 3

Inhibition (%) of viral plaques
(Glycyrrhizic acid 0.5 mg/ml + Different doses of chicken lysozyme)

| Chicken lysozyme/ doses (mg/ml) | 0.2 | 0.4 | 0.6 | 0.8 | 1 |
|---|---|---|---|---|---|
| Inhibition (%) | 72 ± 6 | 83 ± 8 | 85 ± 8 | 87 ± 9 | 88 ± 8 |

As can be seen from Table 3, the associations of glycyrrhizic acid and lysozymes are characterized by a marked synergic effect. For example, in view of the sum of the activities measured separately (Tables 1 and 2), the inhibition (%) expected for an association comprising 0.5 mg/ml of chicken lysozyme and 0.5 mg/ml of glycyrrhizic acid is of about 35–40%. In contrast, the results shown in Table 3 prove that the inhibition (%) of this association is about 84%.

The synergy is confirmed by the FIC index, which in the case in examination is 0.125.

As it is known, the FIC index (fractioned inhibiting concentrations) is obtained by dividing the 50% viral inhibiting concentration of the mixture of the two products by the 50% viral inhibiting dose of each product singly. An FIC index $\leq 0.5$ means that there is a significant synergy between the two products.

EXAMPLE 4

It was carried out as Example 1 except that different amounts of bovine and human lactoferrin were added to the single layers of VERO cells infected with HSV1.

The experimental data obtained in this way are given in Table 4.

TABLE 4

| | $MTD_{50}$* (mg/ml) | $MDI_{50}$** (mg/ml) |
|---|---|---|
| Bovine lactoferrin | 2 | 0.25 |
| Human lactoferrin | 3 | 0.25 |

*Toxicity expressed as a minimum toxic dose on 50% of the cells.
**Dose inhibiting 50% of the viral plaques on VERO cells.

Table 4 shows that the lactoferrins are not very toxic and that their viral action is already very pronounced at levels significantly below toxic ones.

EXAMPLE 5

It was carried out as Example 1 except that 0.5 mg/ml of glycyrrhizic acid and different amounts from 0 to 1 mg/ml of human lactoferrin were added to the single layers of VERO cells infected with HSV1.

The experimental results are shown in Table 5.

TABLE 5

Inhibition (%) of viral plaques
(Glycyrrhizic acid 0.5 mg/ml + Different doses of human lactoferrin)

| H. lactoferrin doses mg/ml | 0 | 0.0075 | 0.015 | 0.031 | 0.062 | 0.125 | 0.250 | 0.5 | 1 |
|---|---|---|---|---|---|---|---|---|---|
| Inhibition (%) | 30 ± 2 | 30 ± 4 | 50 ± 6 | 50 ± 5 | 60 ± 10 | 80 ± 15 | 100 | 100 | 100 |

As can be seen from Table 5, the associations of glycyrrhizic acid and lactoferrin are characterized by a marked synergic effect. For example, in view of the sum of the activity measured separately (Tables 2 and 4), the expected inhibition (%) of an association comprising 0.25 mg/ml of lactoferrin and 0.5 mg/ml of glycyrrhizic acid is of about 65–75%. In contrast, the results shown in Table 5 prove that the inhibition (%) of this association is about 100%.

The synergy is confirmed by the FIC index, which is 0.06.

EXAMPLE 6

It was carried out as Example 1 except that 0.5 mg/ml of glycyrrhizic acid, 0.1 mg/ml of human lactoferrin and different amounts of from 0 to 1 mg/ml of chicken lysozyme were added to the single layers of VERO cells infected with HSV1.

The experimental results are shown in Table 6.

TABLE 6

Inhibition (%) of viral plaques
(Glycyrrhizic acid 0.5 mg/ml and human lactoferrin 0.1 mg/ml + Different doses of chicken lysozme

| Chicken lysozyme/ doses (mg/ml) | 0 | 0.25 | 0.5 | 0.75 | 1 |
|---|---|---|---|---|---|
| Inhibition (%) | 48 ± 2 | 95 ± 5 | 98 ± 2 | 99 ± 1 | 100 |

As can be seen from Table 6, the associations of glycyrrhizic acid, lactoferrin and lysozymes are characterized by a marked synergic effect. For example, in view of the sum of the activity measured separately, the expected inhibition (%) of an association comprising 0.1 mg/ml of lactoferrin, 0.5 mg/ml of glycyrrhizic acid and 0.5 mg/ml of lysozyme is about 65%. In contrast, the results shown in Table 6 show that the inhibition (%) of this association is about 98%.

What is claimed is:

1. A pharmaceutical composition comprising a synergistically effective amount of glycyrrhizic acid and a lactoferrin.

2. The composition according to claim 1, wherein the lactoferrin is human or bovine lactoferrin.

3. The composition according to claim 1, wherein said composition is suitable for treating topical viral infections.

4. The composition according to claim 1, wherein said composition is suitable for treating Herpes Simplex Virus Type I.

5. The composition according to claim 1, which is in the form of a cream.

6. The composition according to claim 1, which is in the form of an ointment.

7. The composition according to claim 1, which is in the form of a medicated plaster.

8. A method of treatment of a topical viral infection, comprising:
    applying a pharmaceutical composition comprising a synergistically effective amount of glycyrrhizic acid and a lysozyme or a lactoferrin to an infected area of a subject in need thereof.

9. The method according to claim 8, wherein the composition comprises the lysozyme.

10. The method according to claim 9, wherein the lysozyme is selected from the group consisting of turkey lysozyme, human lysozyme, chicken lysozyme and lysozyme digested with trypsin.

11. The method according to claim 8, wherein the composition comprises the lactoferrin.

12. The method according to claim 8, wherein said lactoferrin is selected from the group consisting of bovine lactoferrin and human lactoferrin.

13. The method according to claim 8, wherein the subject is infected with a herpes virus.

14. The method according to claim 8, wherein the subject is infected with Herpes Simplex Virus Type I.

15. The method according to claim 8, wherein said pharmaceutical composition is the form of an ointment.

16. The method according to claim 8, wherein said pharmaceutical composition is in the form of a cream.

17. The composition according to claim 8, which is in the form of a medicated plaster.

18. A pharmaceutical composition comprising a synergistically effective amount of glycyrrhizic acid and a lysozyme or a lactoferrin, wherein the composition is in the form of a cream, ointment, or a medicated plaster suitable for topical administration.

* * * * *